(12) United States Patent
Kametani

(10) Patent No.: US 11,439,320 B2
(45) Date of Patent: Sep. 13, 2022

(54) BIOLOGICAL-SOUND ANALYSIS DEVICE, BIOLOGICAL-SOUND ANALYSIS METHOD, PROGRAM, AND STORAGE MEDIUM

(71) Applicant: PIONEER CORPORATION, Tokyo (JP)

(72) Inventor: Ryushin Kametani, Kawagoe (JP)

(73) Assignee: AIR WATER BIODESIGN INC., Hyogo (JP)

(*) Notice: Subject to any disclaimer, the term of this patent is extended or adjusted under 35 U.S.C. 154(b) by 474 days.

(21) Appl. No.: 16/472,166

(22) PCT Filed: Dec. 20, 2017

(86) PCT No.: PCT/JP2017/045774
§ 371 (c)(1),
(2) Date: Jun. 20, 2019

(87) PCT Pub. No.: WO2018/117170
PCT Pub. Date: Jun. 28, 2018

(65) Prior Publication Data
US 2019/0350494 A1 Nov. 21, 2019

(30) Foreign Application Priority Data
Dec. 20, 2016 (JP) .............................. JP2016-246553

(51) Int. Cl.
*A61B 5/08* (2006.01)
*A61B 7/04* (2006.01)
*G10L 25/51* (2013.01)

(52) U.S. Cl.
CPC .................. *A61B 5/08* (2013.01); *A61B 7/04* (2013.01); *G10L 25/51* (2013.01)

(58) Field of Classification Search
CPC .. A61B 5/08; A61B 7/04; A61B 7/003; G10L 25/51
See application file for complete search history.

(56) References Cited

U.S. PATENT DOCUMENTS

2009/0171231 A1* 7/2009 Caro ..................... A61B 7/003
600/529
2010/0262031 A1 10/2010 Fu et al.
2017/0135649 A1 5/2017 Kametani et al.

FOREIGN PATENT DOCUMENTS

JP 2013-123494 6/2013
JP 2015-188638 11/2015
(Continued)

OTHER PUBLICATIONS

English-language machine translation of JP-2015188601-A (Year: 2021).*

(Continued)

*Primary Examiner* — Andrey Shostak
(74) *Attorney, Agent, or Firm* — Nixon & Vanderhye

(57) ABSTRACT

A biological sound analyzing apparatus is provided with: an obtaining device configured to obtain first information regarding biological sounds in a first period; and an outputting device configured to output second information, which indicates a ratio of a generation time in which sounds indicating abnormality of a living body and included in the biological sounds are generated, with respect to the first period, on the basis of the first information. According to the biological sound analyzing apparatus, it is possible to preferably analyze information regarding the sounds indicating the abnormality because it can output the ratio of the generation time of the sounds indicating the abnormality and included in the biological sounds.

11 Claims, 8 Drawing Sheets

(56) References Cited

FOREIGN PATENT DOCUMENTS

JP   2015188601 A  * 11/2015
WO   WO 2016/002004   1/2016

OTHER PUBLICATIONS

International Search Report, PCT/JP2017/045774, dated Mar. 20, 2018.
Extended European Search Report issued in European Patent Application No. 17884714.1 dated Jun. 29, 2020.

* cited by examiner

BIOLOGICAL-SOUND ANALYSIS DEVICE, BIOLOGICAL-SOUND ANALYSIS METHOD, PROGRAM, AND STORAGE MEDIUM

TECHNICAL FIELD

The present invention relates to a biological sound analyzing apparatus and a biological sound analyzing method for analyzing biological sounds, such as, for example, breath sounds, as well as a program and a recording medium.

BACKGROUND ART

For this type of apparatus, there is known an apparatus configured to detect abnormal sounds, i.e., sounds that are different from normal breath sounds, which are included in breath sounds of a living body detected by an electronic stethoscope or the like. For example, Patent Literature 1 discloses a technology/technique in which a plurality of abnormal sounds (adventitious sounds) included in the breath sounds are divided and detected for each sound type.

CITATION LIST

Patent Literature

Patent Literature 1: International Publication No. WO2016/002004

SUMMARY OF INVENTION

Technical Problem

In performing analysis regarding the abnormal sounds included in the biological sounds, for example, a ratio of a period in which the abnormal sounds are generated is detected, by which, for example, the presence/absence of the abnormal sounds can be accurately determined. In the technology/technique disclosed in the Patent Literature 1, however, a ratio of the plurality of abnormal sounds included in the breath sounds can be detected, but reference is not made to the ratio of the period in which the abnormal sounds are generated. Thus, the ratio of the period in which the abnormal sounds are generated cannot be detected only by the technology/technique disclosed in the Patent Literature 1, which is technically problematic.

An example of problems to be solved by the present invention includes the aforementioned technical problem. It is therefore an object of the present invention to provide a biological sound analyzing apparatus and a biological sound analyzing method that can preferably analyze the abnormal sounds included in the biological sounds, as well as a program and a recording medium.

Solution to Problem

The above object of the present invention can be achieved by a biological sound analyzing apparatus provided with: an obtaining device configured to obtain first information regarding biological sounds in a first period; and an outputting device configured to output second information, which indicates a ratio of a generation time in which sounds indicating abnormality of a living body and included in the biological sounds are generated, with respect to the first period, on the basis of the first information.

The above object of the present invention can be achieved by a biological sound analyzing method used by a biological sound analyzing apparatus, the method provided with: an obtaining process of obtaining first information regarding biological sounds in a first period; and an outputting process of outputting second information, which indicates a ratio of a generation time in which sounds indicating abnormality of a living body and included in the biological sounds are generated, with respect to the first period, on the basis of the first information.

The above object of the present invention can be achieved by a program for allowing the biological sound analyzing apparatus to perform the biological sound analyzing method described above.

The above object of the present invention can be achieved by a recording medium on which the program described above is recorded.

DESCRIPTION OF EMBODIMENTS

<1>

Figure 1:
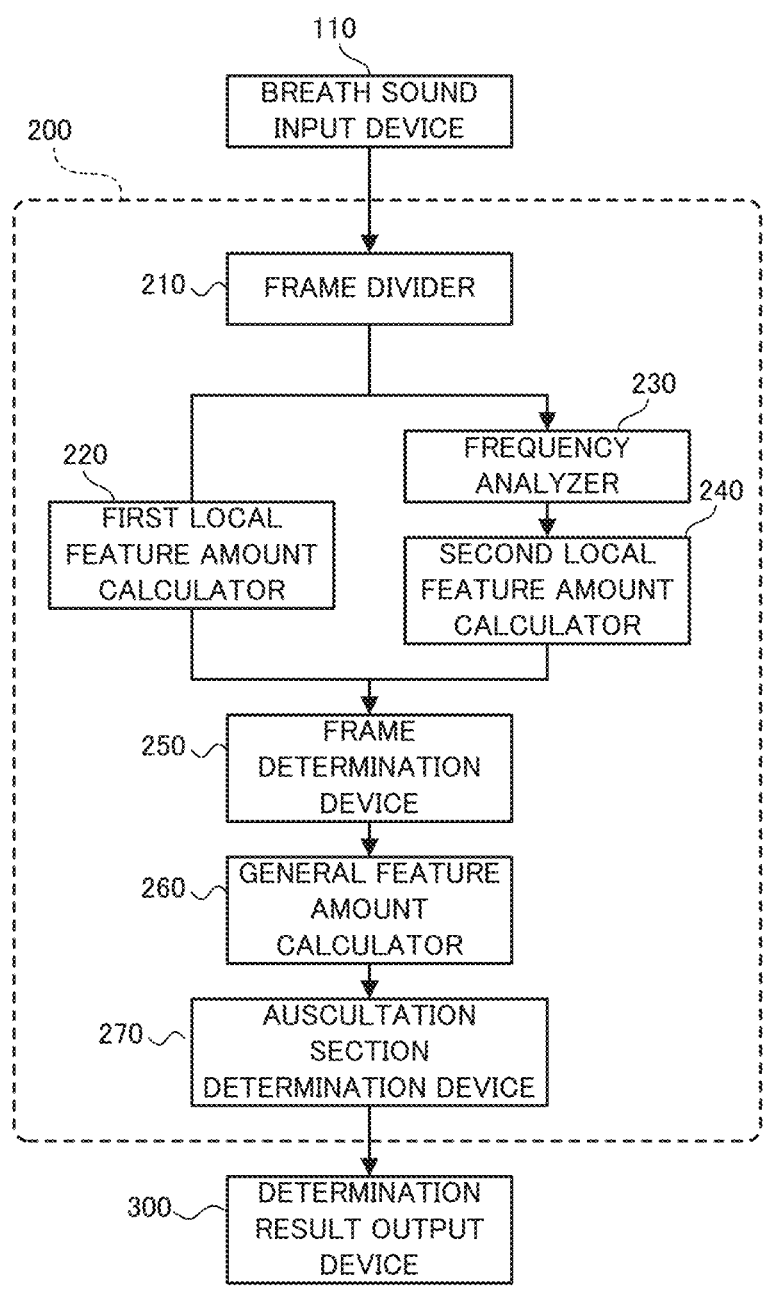
FIG. 1 is a block diagram illustrating a configuration of a biological sound analyzing apparatus according to an example.

A biological sound analyzing apparatus according to an embodiment is provided with: an obtaining device configured to obtain first information regarding biological sounds in a first period; and an outputting device configured to output second information, which indicates a ratio of a generation time in which sounds indicating abnormality of a living body and included in the biological sounds are generated, with respect to the first period, on the basis of the first information.

According to the biological sound analyzing apparatus in the embodiment, in operation thereof, the first information regarding the biological sounds in the first period is obtained. The "biological sounds" may be sounds generated by the living body, which is an inspection subject, and are typically breath sounds. Moreover, the "first information" may be information indicating a change in the biological sounds with time, and may be obtained, for example, as a time-base waveform indicating the biological sounds.

If the first information is obtained, an analysis process using the first information is performed and the second information is outputted, wherein the second information indicates the ratio of the generation time in which the sounds indicating the abnormality of the living body are generated, with respect to the first period. In other words, outputted is the information indicating the ratio of the generation time (or generation period) of the sounds indicating the abnormality, with respect to a period in which the biological sounds are obtained. The "sounds indicating the abnormality" may be sounds that are originally not to be included in the biological sounds (e.g., adventitious sounds).

By using the second information, it is possible to accurately determine, for example, whether or not the biological sounds obtained in the first period include the sounds indicating the abnormality. Specifically, if the ratio of the generation time of the sounds indicating the abnormality is sufficiently large, it can be determined that the sounds indicating the abnormality are surely generated. On the other hand, if the ratio of the generation time of the sounds indicating the abnormality is extremely small, even if there is the generation time in which the sounds indicating the abnormality are generated, this is erroneous detection due to an influence of noise or the like. It is thus possible to determine that the sounds indicating the abnormality are actually not generated.

As explained above, according to the biological sound analyzing apparatus in the embodiment, it is possible to analyze the biological sounds by outputting the ratio of the generation time in which the sounds indicating the abnormality are generated.

<2>

In an aspect of the biological sound analyzing apparatus according to the embodiment, it is further provided with: a division processing device configured to perform a process of dividing the first information into a plurality of frame information for each second period; and a determining device configured to determine whether or not the sounds indicating the abnormality are generated, for each of the plurality of frame information, wherein the outputting device is configured to output, as the second information, a ratio of the frame information in which the sounds indicating the abnormality are generated, with respect to all the frame information that determination is performed by the determining device.

According to this aspect, the obtained first information is firstly divided as the plurality of frame information for each second period. The "second period" is a period indicating a division unit of the frame information, and is set in advance as a period that is shorter than the first period.

If the first information is divided into the plurality of frame information, it is determined whether or not the sounds indicating the abnormality are generated, for each of the plurality of frame information. Then, the ratio of the frame information in which the sounds indicating the abnormality are generated, with respect to all the frame information that the determination is performed, is outputted as the second information.

In this manner, the presence/absence of the sounds indicating the abnormality can be determined by a frame unit. It is thus possible to preferably output the second information, i.e., information indicating a ratio of a generation period in which abnormal sounds are generated.

<3>

In the aspect in which the first information is divided into the plurality of frame information described above, the outputting device may output third information, which indicates a temporal position of the frame information in which the sounds indicating the abnormality are generated.

In this case, it is possible to detect timing in which the sounds indicating the abnormality in the first period are generated, from the temporal position of the frame information in which the sounds indicating the abnormality are generated.

<4>

Alternatively, in the aspect in which the first information is divided into the plurality of frame information, the determining device may determine whether or not the sounds indicating the abnormality are generated, on the basis of waveform information of the biological sounds included in the first information and spectrum information obtained by frequency-analyzing the waveform information.

According to this aspect, by using both the waveform information of the biological sounds and the spectrum information obtained by frequency-analyzing (e.g., by performing a Fast Fourier Transform (FFT) process on) the waveform information, it is possible to more preferably determine whether or not the sounds indicating the abnormality are generated.

<5>

In another aspect of the biological sound analyzing apparatus according to the embodiment, the outputting device is configured to output fourth information, which indicates that the sounds indicating the abnormality are observed, if the ratio of the generation time in which the sounds indicating the abnormality are generated, with respect to the first period, is greater than or equal to a predetermined value.

According to this aspect, it is possible to output the information indicating whether or not the abnormal sounds are actually observed, on the basis of the ratio of the generation time in which the sounds indicating the abnormality are generated. The "predetermined value" may be a threshold value set for determining whether or not the abnormal sounds are generated, and may be determined in advance by advanced simulations or the like.

<6>

In another aspect of the biological sound analyzing apparatus according to the embodiment, the biological sounds are breath sounds, the sounds indicating the abnormality are adventitious sounds, and the outputting device is configured to output the second information for each sound type of the adventitious sounds.

According to this aspect, it is possible to output the information regarding the adventitious sounds (e.g., continuous sounds and discontinuous sounds), which can be included in the breath sounds of the living body, for each sound type of the adventitious sounds.

<7>

A biological sound analyzing method according to an embodiment is a biological sound analyzing method used by a biological sound analyzing apparatus, the method provided with: an obtaining process of obtaining first information regarding biological sounds in a first period; and an outputting process of outputting second information, which indicates a ratio of a generation time in which sounds indicating abnormality of a living body and included in the biological sounds are generated, with respect to the first period, on the basis of the first information.

According to the biological sound analyzing method in the embodiment, as in the biological sound analyzing apparatus in the embodiment described above, it is possible to preferably analyze the biological sounds by outputting the ratio of the generation time in which the sounds indicating the abnormality are generated.

Even the biological sound analyzing method in the embodiment can also adopt the same various aspects as those of the biological sound analyzing apparatus in the embodiment described above.

<8>

A program according to an embodiment allows the biological sound analyzing apparatus to perform the biological sound analyzing method described above.

According to the program in the embodiment, the biological sound analyzing method according to the embodiment described above can be performed. It is thus possible to preferably analyze the biological sounds by outputting the ratio of the generation time in which the sounds indicating the abnormality are generated.

<9>

On a recording medium according to an embodiment, the program described above is recorded.

According to the recording medium in the embodiment, the program according to the embodiment described above can be run. It is thus possible to preferably analyze the biological sounds by outputting the ratio of the generation time in which the sounds indicating the abnormality are generated.

The effect and other advantages of the biological sound analyzing apparatus, the biological sound analyzing method, the program, and the recording medium according to the embodiments will be explained in more detail in the following examples.

EXAMPLES

Hereinafter, a biological sound analyzing apparatus, a biological sound analyzing method, a program, and a recording medium according to examples will be explained in detail with reference to the drawings. In the following examples, a biological sound analyzing apparatus configured to analyze breath sounds will be explained.

<Configuration of Apparatus>

Firstly, a configuration of a biological sound analyzing apparatus according to an example will be explained with reference to FIG. 1. FIG. 1 is a block diagram illustrating the configuration of the biological sound analyzing apparatus according to the example.

In FIG. 1, the biological sound analyzing apparatus according to the example is provided with a breath sound input device 110, a processor 200, and a determination result output device 300.

The breath sound input device 110 is configured to obtain breath sounds of a living body, which is an inspection subject, as a breath sound signal. The breath sound input device 110 may include a microphone using, e.g., an electret condenser microphone (ECM) and a piezo microphone, a vibration sensor, and the like. The breath sound input device 110 may be a sensor configured to obtain the breath sounds of the living body as the breath sound signal, but also may include a device configured to obtain the breath sound signal from the sensor. The breath sound signal obtained by the breath sound input device 110 may be outputted to the processor 200. The breath sound input device 110 is a specific example of the "obtaining device".

The processor 200 may include a plurality of arithmetic circuits, a memory or the like. The processor 200 is provided with a frame divider 210, a first local feature amount calculator 220, a frequency analyzer 230, a second local feature amount calculator 240, a frame determination device 250, a general feature amount calculator 260, and an auscultation section determination device 270.

The frame divider 210 is a specific example of the "division processing device", and is configured to perform a division process of dividing the breath sounds inputted from the breath sound input device 110 into a plurality of frames. The breath sound signal divided by the frame divider 210 may be outputted to the first local feature amount calculator 220 and the frequency analyzer 230.

The first local feature amount calculator 220 is configured to calculate a first local feature amount, on the basis of a waveform of the breath sound signal. A process performed by the first local feature amount calculator 220 will be detailed later. The first local feature amount calculated by the first local feature amount calculator 220 may be outputted to the frame determination device 250.

The frequency analyzer 230 is configured to perform a time frequency analysis process (e.g., a FFT process, etc.) on the breath sound signal inputted from the breath sound input device 110. An analysis result of the frequency analyzer 230 may be outputted to the second local feature amount calculator 240.

The second local feature amount calculator 240 is configured to calculate a second local feature amount, on the basis of the analysis result of the frequency analyzer 230. A process performed by the second local feature amount calculator 240 will be detailed later. The second local feature amount calculated by the second local feature amount calculator 240 may be outputted to the frame determination device 250.

The frame determination device 250 is a specific example of the "determining device", and is configured to determine whether or not each of the frames of the breath sound signal includes sounds indicating abnormality of the living body (hereinafter referred to as "abnormal sounds" as occasion demands). A process performed by the frame determination device 250 will be detailed later. A determination result of the frame determination device 250 may be outputted to the general feature amount calculator 260.

The general feature amount calculator 260 is configured to calculate a ratio of a generation time (or generation period) in which the abnormal sounds are generated, with respect to a period in which the breath sounds are inputted, on the basis of the determination result of the frame determination device 250. Information indicating the ratio of the generation time of the abnormal sounds calculated by the general feature amount calculator 260 may be outputted to the auscultation section determination device 270.

The auscultation section determination device 270 is configured to determine whether or not the breath sounds include the abnormal sounds, on the basis of the ratio of the generation time of the abnormal sounds. A determination result of the auscultation section determination device 270 may be outputted to the determination result output device 300.

The determination result output device 300 is configured as a display, such as, for example, a liquid crystal monitor, and is configured to display various information outputted from the processor 200 as image data.

<Explanation of Operation>

Figure 2:
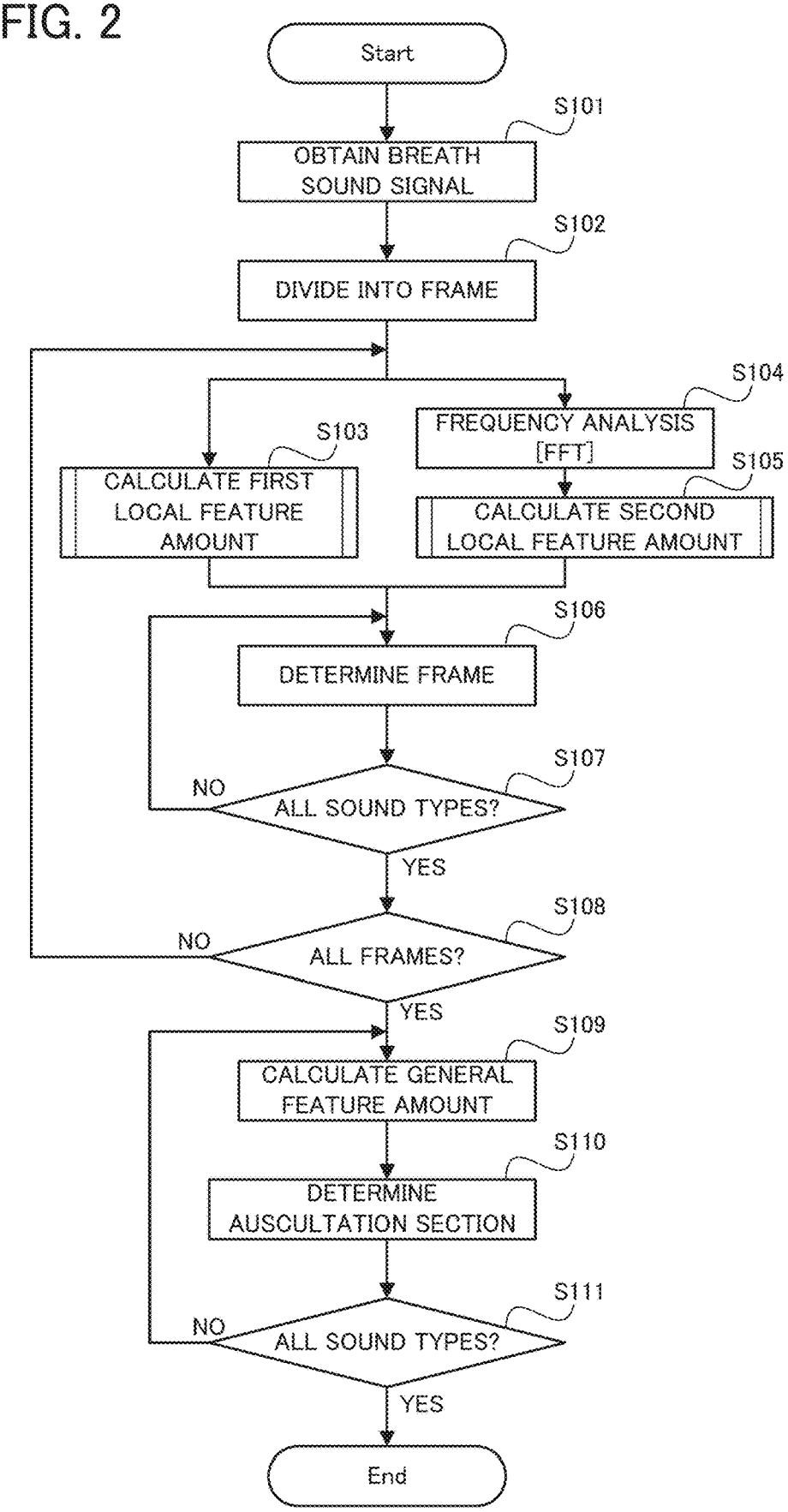
FIG. 2 is a flowchart illustrating a flow of operations of the biological sound analyzing apparatus according to the example.

Next, operations of the biological sound analyzing apparatus according to the example will be explained with reference to FIG. 2. FIG. 2 is a flowchart illustrating a flow of the operations of the biological sound analyzing apparatus according to the example.

As illustrated in FIG. 2, in operation of the biological sound analyzing apparatus according to the example, firstly, the breath sounds are obtained by the breath sound input device 110 (step S101). The breath sound input device 110 outputs the obtained breath sounds to the processor 200, as the breath sound signal (e.g., a waveform indicating a change in the breath sounds with time). The breath sound signal is a specific example of the "first information".

Figure 3:
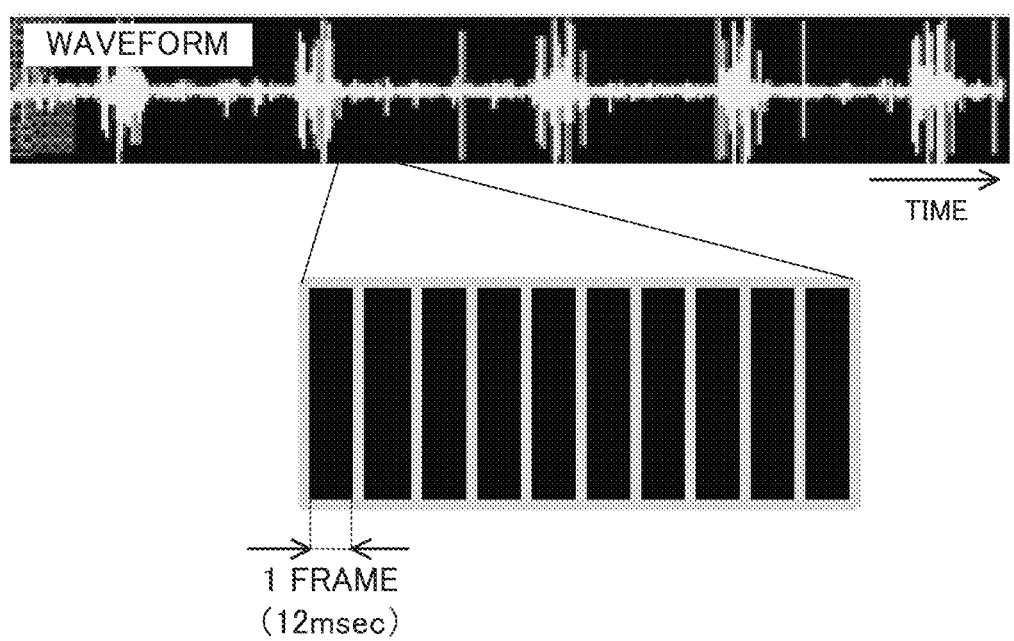
FIG. 3 is a conceptual diagram illustrating a frame division process of a breath sound signal.

Then, the breath sounds are divided into a plurality of frames by the frame divider 210 (step S102). Hereinafter, the frame division of the breath sound signal will be specifically explained with reference to FIG. 3. FIG. 3 is a conceptual diagram illustrating a frame division process of the breath sound signal.

As illustrated in FIG. 3, the breath sound signal is divided into a plurality of frames at predetermined intervals. The frame is set as a processing unit for preferably performing analysis of the breath sounds described later, and a period per frame may be set, for example, to 12 msec.

Back in FIG. 2, the breath sound signal that is divided into the frames is inputted to the first local feature amount calculator 220, and the first local feature amount is calculated (step S103). Moreover, the breath sound signal that is divided into the frames is frequency-analyzed by the frequency analyzer 230, and is inputted to the second local feature amount calculator 240. On the second local feature amount calculator 240, the second local feature amount is calculated on the basis of the frequency-analyzed breath sound signal (e.g., a spectrum indicating frequency characteristics).

Figure 4:
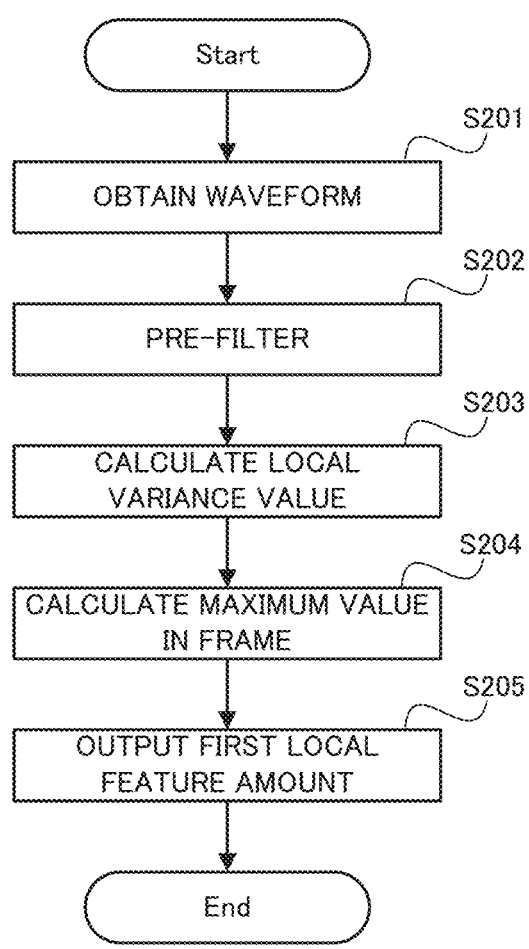
FIG. 4 is a flowchart illustrating a process of calculating a first local feature amount.
Figure 5:
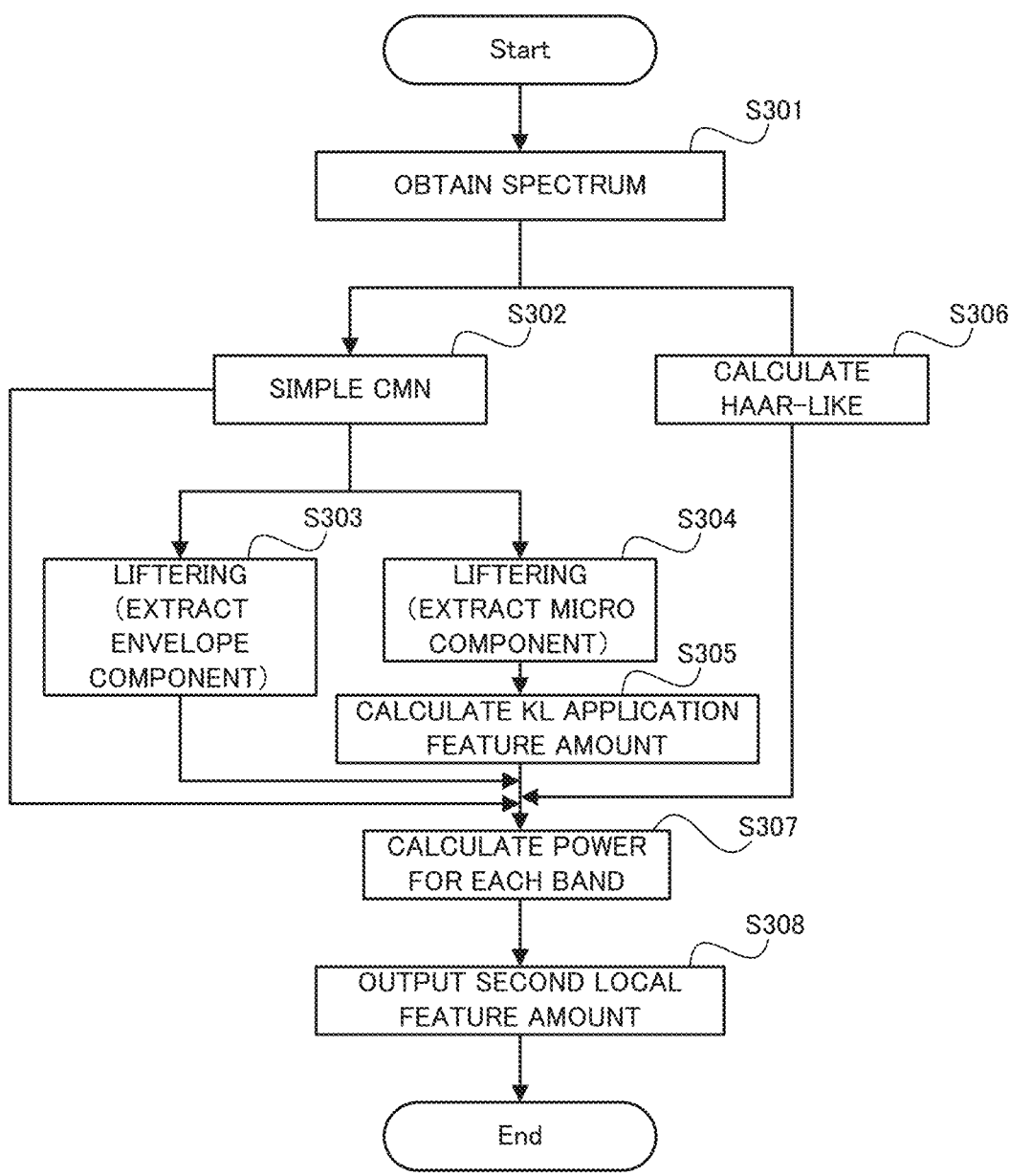
FIG. 5 is a flowchart illustrating a process of calculating a second local feature amount.
Figure 6:
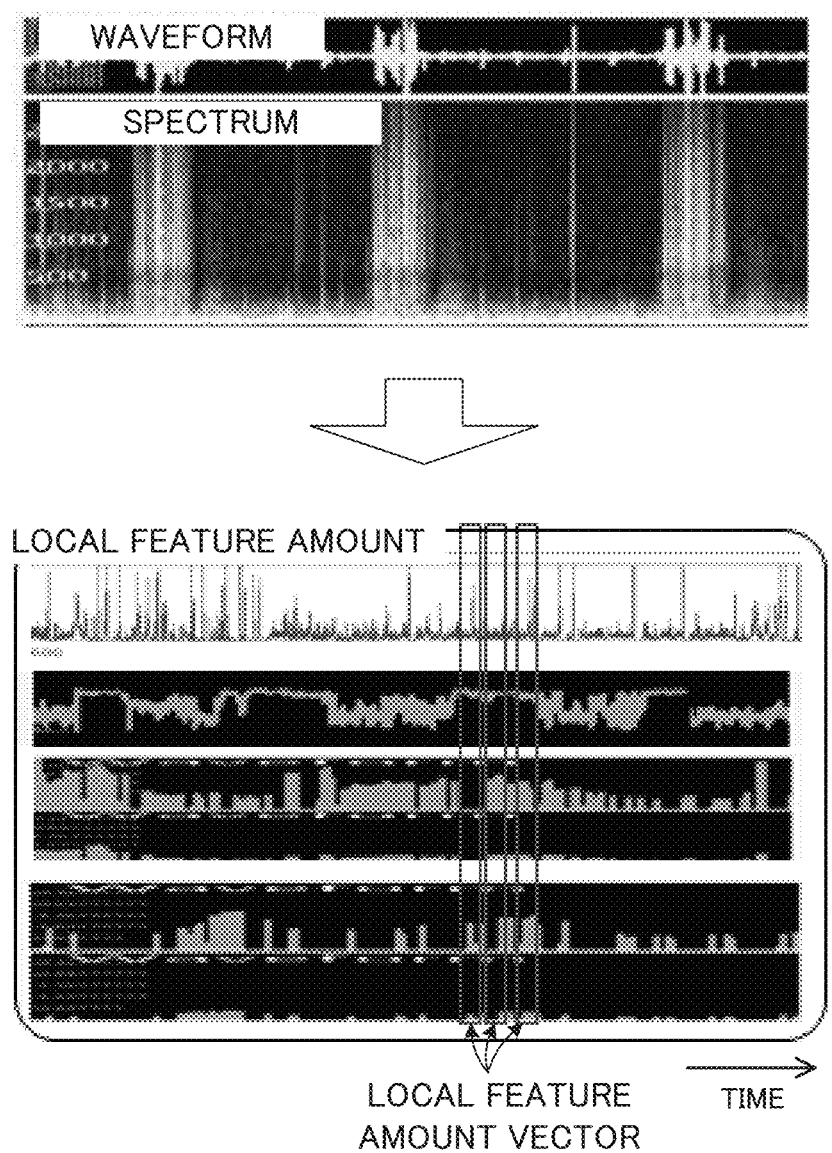
FIG. 6 is a diagram illustrating a local feature amount vector obtained from a waveform and a spectrum.

Hereinafter, a process of calculating the first local feature amount by the first local feature amount calculator 220 and a process of calculating the second local feature amount by the second local feature amount calculator 240 will be explained in detail with reference to FIG. 4 to FIG. 6. FIG. 4 is a flowchart illustrating the process of calculating the first local feature amount. FIG. 5 is a flowchart illustrating the process of calculating the second local feature amount. FIG. 6 is a diagram illustrating a local feature amount vector obtained from a waveform and a spectrum.

As illustrated in FIG. 4, in calculation of the first local feature amount, firstly, the waveform of the breath sound signal is obtained (step S201), and a pre-filter process is performed thereon (step S202). The pre-filter process may be, for example, a process using a high pass filter, and can remove an unnecessary component included in the breath sound signal.

Then, a local variance value is calculated by using the breath sound signal on which the pre-filter process is performed (step S203). The local variance value may be calculated, for example, as a first variance value indicating variance of the breath sound signal in a first period w1, and as a second variance value indicating variance of the breath sound signal in a second period w2, which includes the first period w1. The local variance value calculated in this manner functions as the local feature amount for determining, particularly, discontinuous sounds (e.g., coarse crackles) from among the abnormal sounds.

When the local variance value is calculated, a maximum value of the local variance value in each of the frames of the breath sound signal is calculated (step S204), and is outputted as the first local feature amount (step S205).

As illustrated in FIG. 5, in calculation of the second local feature amount, firstly, the spectrum obtained by the frequency analysis is obtained (step S301), and a cepstral mean normalization (CMN) process is performed (step S302). The CMN process can remove regularly convoluted characteristics, such as a sensor and an environment, from the breath sound signal.

For the breath sound signal on which the CMN process is performed, a liftering process for extracting an envelope component (step S303) and a liftering process for extracting a micro component (step S304) are further performed. The liftering process may be a process of cutting a predetermined quefrency component from a cepstrum.

According to the CMN process and the liftering process described above, it is possible to make it easy to determine the discontinuous sounds (e.g., rhonchi, wheezes, fine crackles, etc.), which are buried in the other biological sounds. The CMN process and the liftering process are the existing technologies/techniques, and a detailed explanation thereof will be thus omitted here.

For the breath sound signal on which the liftering process for extracting the micro component is performed, an enhancement process using a KL information amount is performed to calculate the feature amount. The KL information amount is a parameter calculated by using an observed value P and a reference value Q (e.g., a theoretical value, a model value, a predicted value, etc.). When the observed value P that is characteristic of the reference value Q appears, the KL information amount is calculated as a large value. According to the process using the KL information amount, a tone-based component (i.e., a component for determining the discontinuous sounds) included in the breath sounds is enhanced and becomes clear.

On the other hand, for the spectrum obtained by the frequency analysis, HAAR-LIKE features are also calculated (step S306). The HAAR-LIKE features are technologies/techniques used mainly in a field of image processing. Here, the HAAR-LIKE features are calculated from the spectrum in the same manner by associating an amplitude value for each frequency with a pixel value in the image processing. The calculation of the HAAR-LIKE features is the existing technology/technique, and a detailed explanation thereof will be thus omitted here.

As described above, when the various processes are performed on the breath sound signal and the plurality of feature amounts are calculated for each frequency, an average value is calculated for each frequency band (step S307), and is outputted as the second local feature amount (step S308).

As illustrated in FIG. 6, a plurality of types of local feature amounts, i.e., the first local feature amount and the second local feature amount, are obtained by the aforementioned processes from the waveform and the spectrum of the breath sound signal. They are outputted as a local feature amount vector for each frame.

Back in FIG. 2 again, the generation of the abnormal sounds is determined by a frame unit, by using the calculated local feature amount vector (step S106). The determination of the abnormal sounds for each frame (hereinafter referred to as a "frame determination process" as occasion demands) is performed on each sound type if there are a plurality of abnormal sounds that are analysis targets. Thus, if the frame determination process is ended, it is determined whether or not the frame determination process is completed for all the sound types (step S107). If the frame determination process is not completed for all the sound types (the step S107: NO), the frame determination process is performed again on the sound type that is not determined yet.

On the other hand, if frame determination process is completed for all the sound types (the step S107: YES), it is determined whether or not the determination is completed for all the frames of the breath sound signal obtained (step S108). If it is determined that the determination is not completed for all the frames (the step S108: NO), the step S103 and the process after the step S104 are performed again. By repeating the process in this manner, the frame determination process is performed on all the sound types and all the frames.

Figure 7:
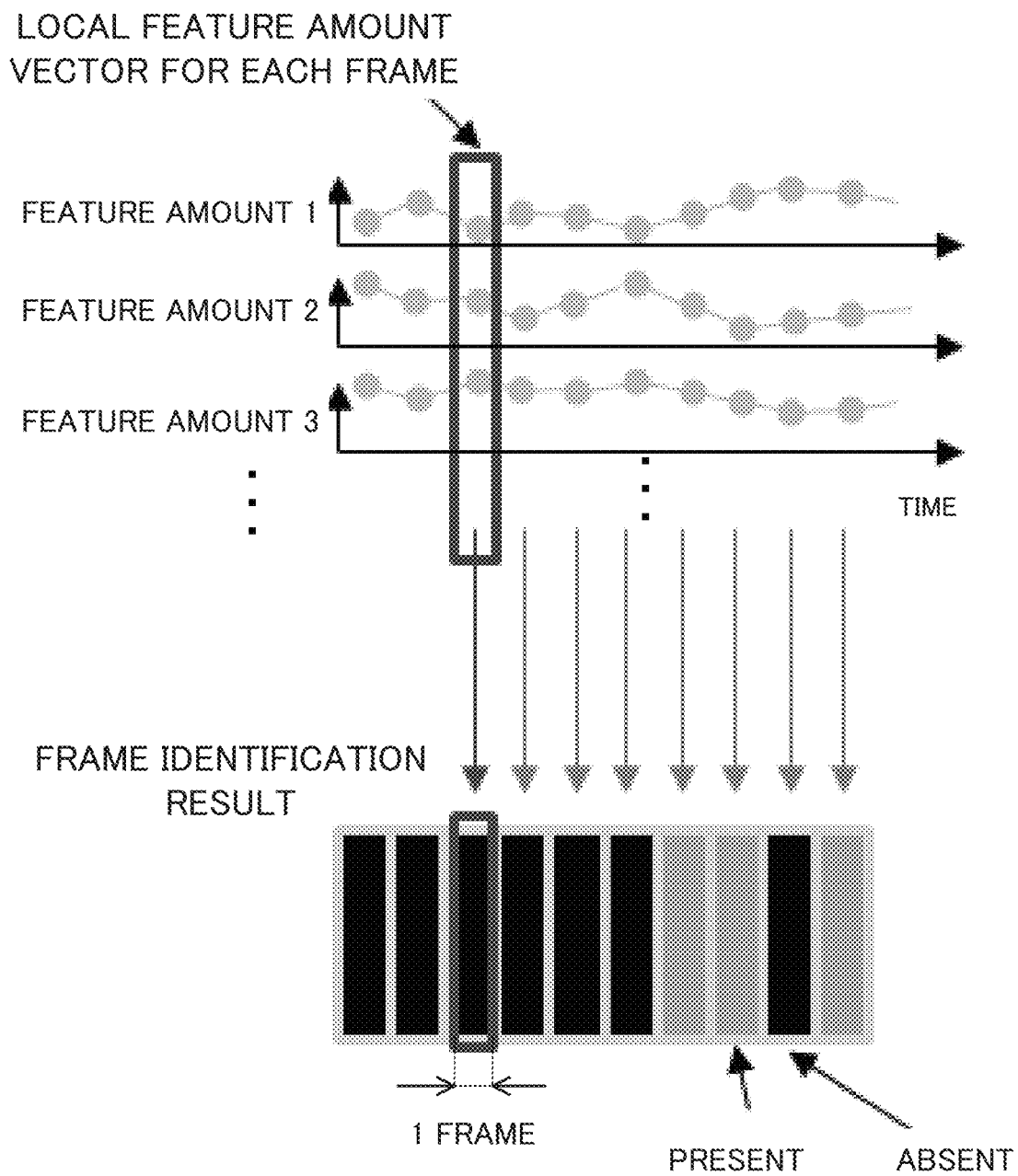
FIG. 7 is a conceptual diagram illustrating an abnormal sound determination process for each frame, using the local feature amount vector.

Hereinafter, the frame determination process by the frame determination device 250 will be explained in detail with reference to FIG. 7 and FIG. 8. FIG. 7 is a conceptual diagram illustrating an abnormal sound determination process for each frame, using the local feature amount vector.

Figure 8:
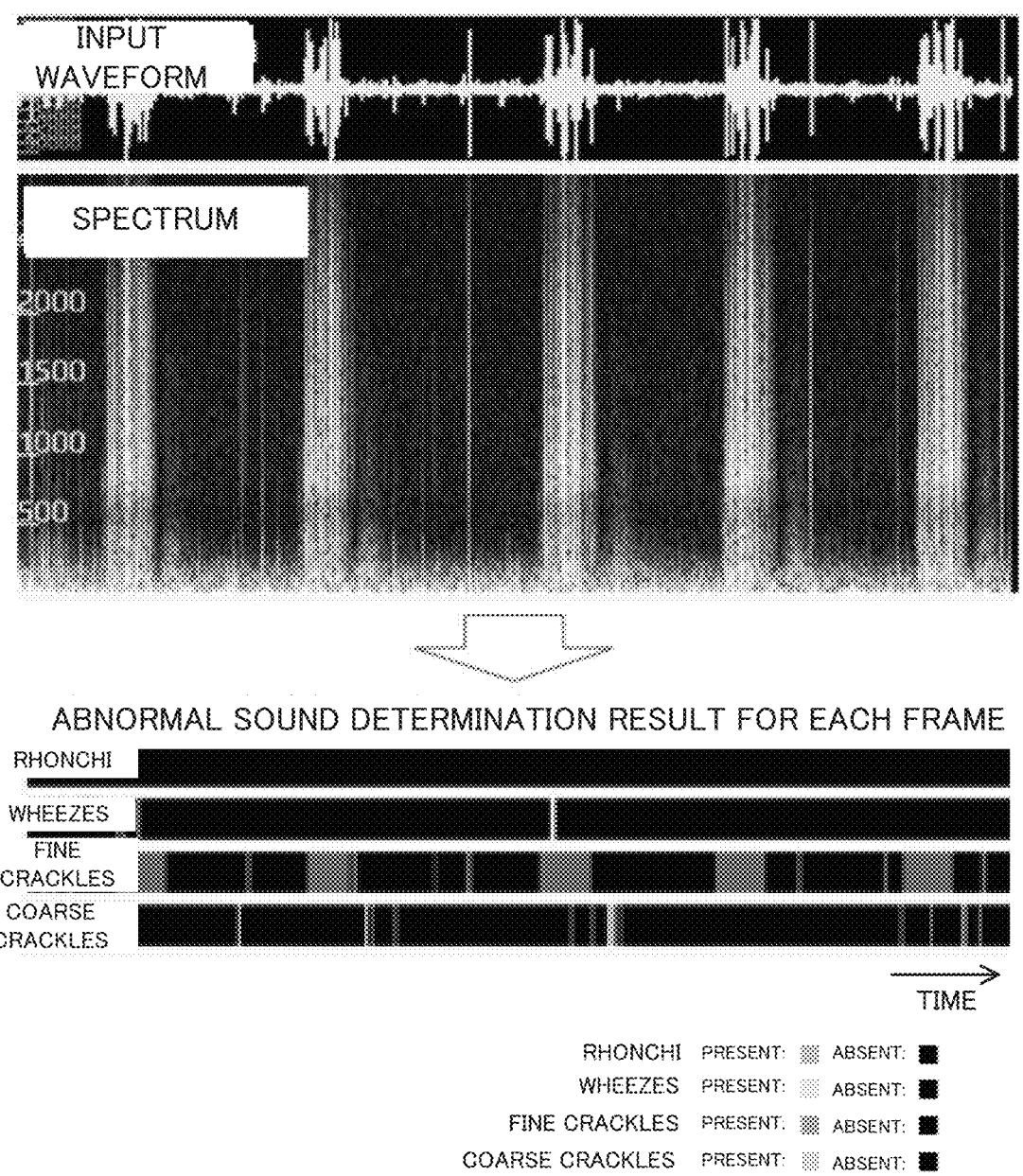
FIG. 8 is a diagram illustrating an abnormal sound determination result for each frame, for each sound type.

FIG. 8 is a diagram illustrating an abnormal sound determination result for each frame, for each sound type.

As illustrated in FIG. 7, the frame determination process is performed on the basis of the local feature amount vector for each frame, which includes the plurality of feature amounts. In the frame determination process, the local feature amount vector corresponding to the abnormal sounds obtained by advanced learning or the like (i.e., the local feature amount vector that is a determination reference) and the actually obtained local feature amount vector are compared, and the presence/absence of the abnormal sounds is determined by the frame unit.

As illustrated in FIG. 8, on the biological sound analyzing apparatus according to the example, the presence/absence of each of rhonchi, wheezes, fine crackles, and coarse crackles is determined by the frame unit, as the abnormal sounds (or adventitious sounds) included in the breath sounds. In the example illustrated in FIG. 8, the generation of rhonchi is hardly detected, but the generation of wheezes, fine crackles, and coarse crackles is detected in some period. In particular, the generation of fine crackles is detected in a relatively large amount of period of time.

According to the frame determination process described above, it is possible to detect a temporal position (in other words, timing) of the frame in which the abnormal sounds are generated. A determination result of the frame determination process is a specific example of the "third information".

Back in FIG. 2 again, if it is determined that the frame determination process is completed for all the frames (the step S108: YES), the ratio of the generation time in which the abnormal sounds are generated, with respect to a period in which the breath sounds are obtained, is calculated for each sound type, by the general feature amount calculator 260 (step S109). The ratio of the generation time in which the abnormal sounds are generated is a specific example of the "second information", and is calculated, for example, as a ratio of the number of the frames in which the abnormal sounds are determined to be generated, with respect to the number of all the frames.

Then, on the auscultation section determination device 270, it is determined whether or not the abnormal sounds are generated in the period in which the breath sounds are obtained (in other words, in an auscultation section), on the basis of the ratio of the generation time in which the abnormal sounds are generated (step S110). Specifically, the auscultation section determination device 270 may determine that the abnormal sounds are generated if the ratio of the generation time in which the abnormal sounds are generated is greater than or equal to a predetermined value, and may determine that the abnormal sounds are not generated if the ratio of the generation time in which the abnormal sounds are generated is less than the predetermined value. A determination result of the auscultation section determination device 270 is a specific example of the "fourth information".

This is the end of the process performed by the biological sound analyzing apparatus according to the example. A series of the steps is repeated every time the breath sounds are obtained by an amount corresponding to a predetermined period.

<Effect of Example>

On the biological sound analyzing apparatus according to the example, the plurality of local feature amount vectors are used to determine the generation of the abnormal sounds for each frame. It is thus possible to detect generation timing of the abnormal sounds. However, if the generation of the abnormal sounds is determined only by the frame unit, it is possibly determined that the abnormal sounds are generated in some frame, for example, due to an influence of noise or the like, even though the abnormal sounds are actually not generated.

In the example, however, the ratio of the generation time in which the abnormal sounds are generated, with respect to the period in which the breath sounds are obtained, is calculated, and it is thus possible to detect the generation of the abnormal sounds, more accurately.

The present invention is not limited to the aforementioned embodiments and examples, but various changes may be made, if desired, without departing from the essence or spirit of the invention which can be read from the claims and the entire specification. A biological sound analyzing apparatus, a biological sound analyzing method, a program, and a recording medium that involve such changes are also intended to be within the technical scope of the present invention.

DESCRIPTION OF REFERENCE NUMERALS AND LETTERS

110 breath sound input device
200 processor
210 frame divider
220 first local feature amount calculator
230 frequency analyzer
240 second local feature amount calculator
250 frame determination device
260 general feature amount calculator
270 auscultation section determination device
300 determination result output device

The invention claimed is:

1. A biological sound analyzing apparatus, comprising:
a processor, in communication with a memory; and
an output device configured to display information output from the processor as image data,
said processor configured to function at least as:
  an obtainer configured to obtain first information regarding biological sounds in a first period, said first information obtained as waveform information of a sound signal to be processed by said processor and indicating change of said biological sounds in said first period;
  a division processor configured to perform a process of dividing the first information into a plurality of frame information according to a plurality of second periods, each of said second periods being shorter than the first period;
  a determiner configured to determine, for each one of the plurality of frame information, whether or not sounds indicating abnormality of a living body and included in the biological sounds are generated; and
  an outputter configured to output second information to said output device, said second information indicating a ratio of a generation time in which the sounds indicating the abnormality are generated, with respect to the first period, on the basis of the first information, said second information is calculated as a ratio of the frame information in which the sounds indicating the abnormality are generated, with respect to all the frame information for which determination is performed by said determiner,
wherein the determiner determines whether or not sounds are generated indicating the abnormality included in the biological sounds, for each one of the plurality of frame information, by performing a pre-filter process on the waveform information of the sound signal and calculating a maximum value of a local variance in each frame of the plurality of frame information according to the second period to determine a first local feature amount, and by obtaining a spectrum on the waveform information of the sound signal and performing a cepstral mean normalization process, performing a liftering process to extract an envelope component, and a liftering process to extract a micro component to determine a second local feature amount, the first and second local feature amounts used to determine said second information indicating the ratio of the generation time in which the sounds indicating abnormality are generated, with respect to the first period, for detecting the generation of the abnormal sounds in the biological sounds.

2. The biological sound analyzing apparatus according to claim 1, wherein said outputter is further configured to output third information, which indicates a temporal position of the frame information in which the sounds indicating the abnormality are generated.

3. The biological sound analyzing apparatus according to claim 1, wherein said determiner is configured to determine whether or not the sounds indicating the abnormality are generated based on waveform information of the biological sounds included in the first information and spectrum information obtained by frequency-analyzing the waveform information.

4. The biological sound analyzing apparatus according to claim 1, wherein said outputter is configured to further output an indication that the sounds indicating the abnormality are observed when the ratio of the generation time in which the sounds indicating the abnormality are generated, with respect to the first period, is greater than or equal to a predetermined value.

5. The biological sound analyzing apparatus according to claim 1, wherein:
the biological sounds are breath sounds,
the sounds indicating the abnormality are adventitious sounds, and
said outputter is configured to output the second information for each sound type of the adventitious sounds.

6. A biological sound analyzing method implemented by a biological sound analyzing apparatus that includes at least a processor, a memory, and an output device configured to display information output from the processor as image data, said method comprising:
obtaining first information regarding biological sounds in a first period, said first information obtained as waveform information of a sound signal to be processed by said processor and indicating change of said biological sounds in said first period;
dividing the first information into a plurality of frame information according to a second period, said second period being shorter than the first period;
determining whether or not sounds indicating abnormality of a living body and included in the biological sounds are generated, for each one of the plurality of frame information; and
outputting second information to said output device, said second information indicating a ratio of a generation time in which the sounds indicating the abnormality are generated, with respect to the first period, on the basis of the first information,
wherein the output second information is a ratio of the frame information in which the sounds indicating the abnormality are generated, with respect to all the frame information for which determination is performed, and
wherein the determining of whether or not sounds are generated indicating the abnormality included in the biological sounds comprises, for each one of the plurality of frame information, performing a pre-filter process on the waveform information of the sound signal and calculating a maximum value of a local variance in each frame of the plurality of frame information according to the second period to determine a first local feature amount, and obtaining a spectrum on the waveform information of the sound signal and performing a cepstral mean normalization process, performing a liftering process to extract an envelope component, and a liftering process to extract a micro component to determine a second local feature amount,
the first and second local feature amounts used to determine said second information indicating the ratio of the generation time in which the sounds indicating abnormality are generated, with respect to the first period, for detecting the generation of the abnormal sounds in the biological sounds.

7. A non-transitory computer readable recording medium on which a program is recorded, said program configured to cause a processor of a biological sound analyzing apparatus to perform the biological sound analyzing method according to claim 6.

8. The biological sound analyzing apparatus according to claim 1, wherein the obtainer comprises a sound input device that registers the sound signal and outputs the sound signal to the processor as the waveform information to be processed by said processor.

9. The biological sound analyzing apparatus according to claim 8, wherein the sound input device comprises a microphone.

10. The biological sound analyzing method according to claim 6, wherein the first information is obtained by way of a sound input device that registers the sound signal and outputs the sound signal to the processor as the waveform information to be processed by said processor.

11. The biological sound analyzing method according to claim 10, wherein the sound input device comprises a microphone.

* * * * *